US00PP17700P3

(12) United States Plant Patent
Ichiba

(10) Patent No.: US PP17,700 P3
(45) Date of Patent: May 8, 2007

(54) ***ASTER TATARICUS* PLANT NAMED 'BLUE LAKE BLIM'**

(50) Latin Name: *Aster tataricus*
Varietal Denomination: Blue Lake Blim

(75) Inventor: Kaori Ichiba, Yamanashi (JP)

(73) Assignee: Miyoshi & Co. Ltd., Tokyo (JP)

( * ) Notice: Subject to any disclaimer, the term of this patent is extended or adjusted under 35 U.S.C. 154(b) by 295 days.

(21) Appl. No.: 10/627,022

(22) Filed: Jul. 25, 2003

(65) Prior Publication Data

US 2004/0019947 P1 Jan. 29, 2004

(51) Int. Cl.
*A01H 5/00* (2006.01)

(52) U.S. Cl. ..... Plt./355
(58) Field of Classification Search ..... Plt./355
See application file for complete search history.

(56) References Cited

PUBLICATIONS

GTITM UPOVROM Citation for 'Violet Lake Blim' as per JP PBR 14194; Dec. 25, 2001.*

* cited by examiner

*Primary Examiner*—Kent Bell
(74) *Attorney, Agent, or Firm*—Christie, Parker & Hale, LLP

(57) ABSTRACT

A new plant variety of *Aster tataricus* characterized by its late spring to early summer bloom season, the distinct violet cast of its ray florets and its compactness, reaching a mature height of 40 to 50 cms tall in flower.

1 Drawing Sheet

Botanical classification: *Aster tataricus* L. 'Blue Lake Blim'.

BACKGROUND OF THE INVENTION

The present invention relates to a new and distinct variety of *Aster tataricus* L. f., which was developed in a controlled breeding program in Kobuchizawa, Gumma Prefecture, Japan by Mr. Shoji Hatano. The varietal denomination of the new variety is 'Blue Lake Blim'.

The genus *Aster* is included in the family Compositae that comprises about 1,300 genera and 21,000 species of herbs, sometimes shrubs, or occasionally trees in tropics, mostly temperate in origin. *Aster* comprises approximately 250 species of mainly herbaceous perennials, though some annuals and biennials, originating in South America, Eurasia, Africa and Asia, many of which possess desirable ornamental characteristics.

*Aster tataricus* is an extremely variable clumping to rhizomatus perennial native to Japan, Korea, Manchuria, northern China, Mongolia and Siberia. It is typically about 2 meters tall.

SUMMARY OF THE INVENTION

The new variety was discovered in a controlled breeding program and differs from its parents by its late spring to early summer bloom season, the distinct violet cast of its ray florets and its compactness, reaching a mature height of 40 to 50 cms tall in flower. *Aster tataricus* 'Blue Lake Blim' differs from *Aster tataricus* 'Blue Lake' (U.S. Plant Pat. No. 15,775) by being 20% shorter, blooming two weeks later and violet flower color. Asexual reproduction of the new variety by division and flower stem cuttings, performed in Kobuchizawa, Gumma Prefecture, Japan have confirmed that the distinctive characteristics of the new variety are stable and transmitted to succeeding generations, and the new variety reproduces true to type.

COMPARISON WITH PARENTS

'Blue Lake Blim' is distinguished from its parents and all other varieties of *Aster tataricus* of which I am aware by its spring to early summer bloom season, the distinct violet cast of its ray florets and its compactness, reaching a mature height of 40 to 50 cms tall in flower.

BRIEF DESCRIPTION OF ILLUSTRATION

The accompanying illustration shows a plant of the new cultivar showing the colors as true as is reasonably possible to make in an illustration of this character. The photographic illustration depicts a plant of the new cultivar.

DETAILED DESCRIPTION OF THE NEW VARIETY

'Blue Lake Blim' has not been observed under all possible environmental, cultural and light conditions. The following observations and descriptions are of approximately one-year-old plants in 1-gallon nursery containers, grown in Kitakoma-gun, Yamanashi, Japan. In this description, color references are to The Royal Horticultural Society Colour Chart (2001) and terminology used in the color descriptions herein refers to plate numbers in this color chart. Phenotypic expression may vary with light intensity, cultural and environmental conditions.

Classification:

*Botanical.*—*Aster tataricus* L. 'Blue Lake Blim'.

*Parentage.*—Female or Seed Parent: *Aster tataricus* L. 'Blue Lake' (U.S. Plant patent Applied For; application Ser. No. 10/357,937; filed Feb. 3, 2003).

*Male or pollen parent.*—Unknown (unpatented).

*Propagation.*—Division and flower stem cuttings.

*Time to rooting.*—Spring: About 21 days at a temperature of 21° C. Winter: About 28 days at a temperature of 18° C.

*Rooting habit.*—Fine, fibrous, well-branched.

Plant description:

*Appearance.*—Herbaceous perennial with mounded growth habit with upright flower stems. Freely and uniformly flowering; violet-colored inflorescences.

*Size.*—Height: In flower, 40 to 50 cm; vegetative stage, 12 to 18 cm.

*Width.*—30 to 40 cm.

*Habit.*—Mounding perennial, clumping to slightly rhizomatous, with a basal rosette of foliage and cauline leaves ascending the stems.

*Branching.*—Leaves radiate from a stout caudex at or below the soil surface.

*Hardiness.*—USDA Zone 4 (−30° F. to −20° F.).

*Growth rate.*—Moderate to vigorous.

Foliage description:

*Shape.*—Oblanceolate to spatulate.

*Apex.*—Acute.

*Base.*—Attenuate.

*Margin.*—Irregularly dentate.

*Leaf size.*—Mature: Basal leaves: 6 to 7 cm wide; 12 to 30 cm long. Cauline leaves: 1.5 to 3.5 cm wide; 2 to 17 cm long.

*Juvenile.*—2 to 3 cm wide; 6 to 7 cm long.

*Arrangement.*—Alternate on the stem, occasionally forming false whorls at the ends of shoots or subtending an inflorescence.

*Substance.*—Coreaceous.

*Texture.*—Bullate, especially the basal leaves; scabrous above and beneath, more scabrous above.

Color:

*Mature foliage.*—Upper Surface: Near Green Group 136A–B. Lower Surface: Near Green Group 136A–B.

*Young foliage.*—Upper Surface: Near Yellow-Green Group 146A. Under Surface: Near Yellow-Green Group 147C.

*Venation.*—Pattern: Upper and Lower Surfaces: Alternately pinnate, occasionally opposite near base.

Color:

*New foliage.*—Upper Surface: near Yellow-Green Group 148B. Under Surface: near Yellow-Green Group 146B.

*Mature foliage.*—Upper Surface: near Yellow-Green Group 148C.

*Under surface.*—Near Yellow-Green Group 146D.

*Flower description.*—Appearance: Typical composite "daisy" flowers borne in a loose many-flowered corymb, the up-facing heads held on stiff peduncles, terminal and in leaf axils along the stem. Disc and ray florets arranged acropetally on a capitulum.

*Flowering response.*—Under natural conditions, plants flower from late spring through fall.

*Quantity of inflorescences.*—Inflorescences form at every leaf axil. Freely flowering, usually about 65 to 80 inflorescences per plant per season, and from 18 to 25 inflorescences per stem.

*Inflorescence size.*—Diameter: About 3 cm. Depth (height): About 1 cm. Disc diameter: About 8 mm. Fragrance: None.

*Inflorescence bud.*—Shape: Ovoid. Length: About 1 cm. Diameter: About 5 mm. Color: Near Purple Group N78C.

*Ray florets.*—Quantity of ray florets/inflorescence: From about 16 to 22 per inflorescence. Shape: Elliptic. Apex: Rounded. Base: Attenuate. Margin: Entire. Length: About 1.2 to 1.6 cm. Width: About 4 to 6 mm. Texture: Satiny, smooth and glabrous. Color: Near violet group N87B–C.

*Disc florets.*—Quantity: About 35 to 40 per inflorescence. Shape: Tubular. Length: About 6 mm. Width: About 2 mm. Color: Near Yellow Group 7C.

*Phyllaries.*—Appearance: Leaf-like. Quantity: Approximately 25. Shape: Linear. Apex: Acute. Base: Truncate. Margin: Entire Texture: Smooth. Color: Upper Surface: Near Green Group 139C; Lower Surface: Near Green Group 139C.

*Peduncle.*—Aspect: Angled about 45°. Strength: Strong. Length: Apical peduncle: About 2 cm. Fourth peduncle: About 5 cm. Seventh peduncle: About 6 cm. Texture: Coarse. Color: Near Green Group 138B.

*Lastingness of inflorescence.*—On Plant: 6 to 8 weeks. Cut Flower: Up to 2 weeks.

*Lastingness of individual bloom.*—On Plant: 2 weeks. Cut Flower: 5 days.

*Time to produce flowering plant.*—Approximately 6 to 8 weeks from a rooted division canned into a #1 nursery container.

Reproductive organs:

*Androecium.*—Present on disc florets only.

*Pollen.*—Scarce.

*Pollen color.*—Near Yellow Group 9B.

*Gynoecium.*—Present on both ray and disc florets.

*Style length.*—About 3 mm.

*Stigma color.*—Near Yellow Group 10C.

*Pistils.*—1 per floret.

Seed production: Seed production has not been observed.

Disease resistance: Plants of 'Blue Lake Blim' have not been observed to be resistant to pathogens common to *Asters*.

I claim:

1. A new plant variety of *Aster tataricus* of the variety substantially as shown and described.

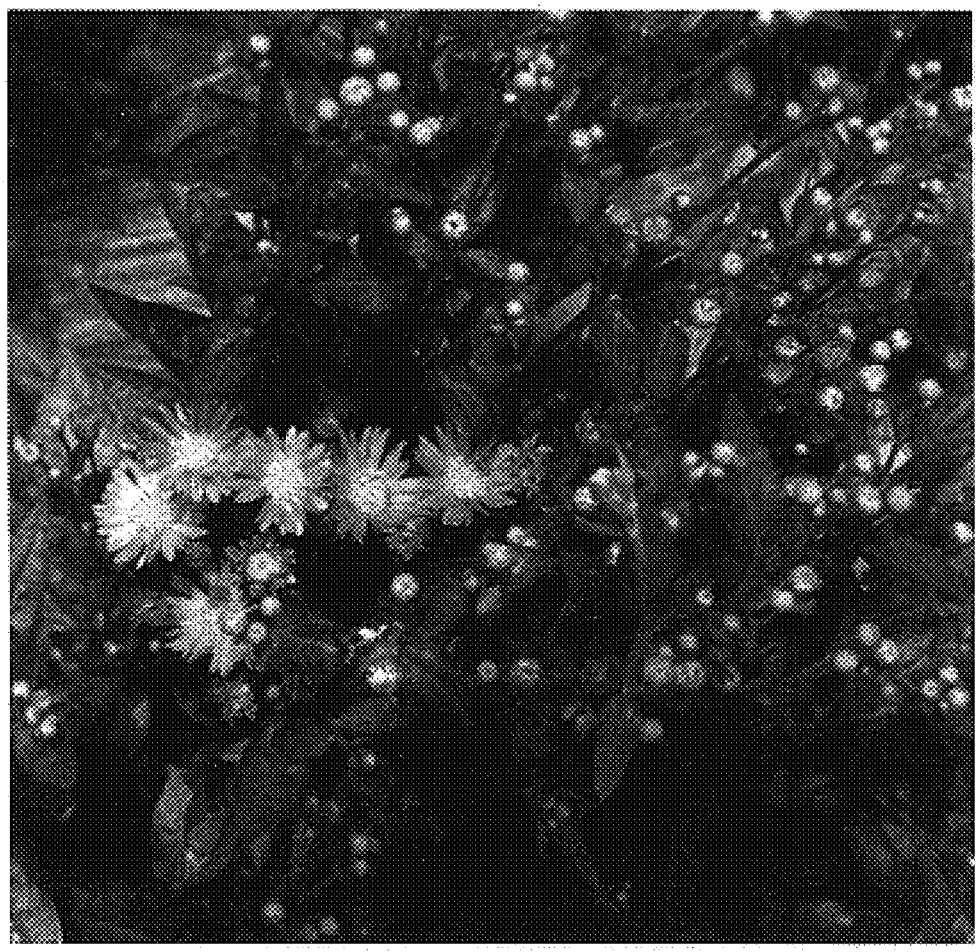

* * * * *